US006274796B1

(12) United States Patent
Croughan

(10) Patent No.: US 6,274,796 B1
(45) Date of Patent: *Aug. 14, 2001

(54) HERBICIDE RESISTANT RICE

(75) Inventor: Timothy P. Croughan, Crowley, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/351,889

(22) Filed: Jul. 13, 1999

Related U.S. Application Data

(63) Continuation of application No. 09/029,109, filed as application No. PCT/US97/07092 on Apr. 28, 1997, now Pat. No. 5,952,553, which is a continuation-in-part of application No. 08/639,793, filed on Apr. 29, 1996, now Pat. No. 5,773,704.

(51) Int. Cl.$^7$ ................................ A01H 5/00; A01H 4/00; A01H 3/00

(52) U.S. Cl. ...................... 800/320.2; 800/300; 800/295; 800/298

(58) Field of Search ................................... 800/295, 300, 800/298, 320.2

(56) References Cited

U.S. PATENT DOCUMENTS

| | | |
|---|---|---|
| Re. 35,661 | 11/1997 | Thill . |
| 4,443,971 | 4/1984 | Chaleff . |
| 4,761,373 | 8/1988 | Anderson et al. ................ 435/172.3 |
| 4,774,381 | 9/1988 | Chaleff et al. . |
| 5,013,659 | 5/1991 | Bedbrook et al. ................ 435/172.3 |
| 5,084,082 | 1/1992 | Sebastian . |
| 5,304,732 | 4/1994 | Anderson et al. . |
| 5,331,107 | 7/1994 | Anderson et al. . |
| 5,545,822 | 8/1996 | Croughan ............................ 800/235 |
| 5,605,011 | 2/1997 | Bedbrook et al. . |
| 5,633,437 | 5/1997 | Bernasconi et al. . |
| 5,718,079 | 2/1998 | Anderson et al. . |
| 5,736,629 | 4/1998 | Croughan ............................ 800/235 |
| 5,767,361 | 6/1998 | Dietrich . |
| 5,767,366 | 6/1998 | Sathasivan ........................... 800/205 |
| 5,773,703 | 6/1998 | Croughan ............................ 800/235 |
| 5,773,704 | 6/1998 | Croughan ............................ 800/235 |
| 5,859,348 | 1/1999 | Penner et al. . |

FOREIGN PATENT DOCUMENTS

| | | |
|---|---|---|
| 0 965 265 A2 | 12/1999 | (EP) . |
| 90/14000 | 11/1990 | (WO) . |
| 92/08794 | 5/1992 | (WO) . |

OTHER PUBLICATIONS

U.S. Pat. application No. 09/029,109, Croughan et al., filed Feb. 1998.

Croughan, T., "Application of Tissue Culture Techniques to the Development of Herbicide Resistant Rice," *Louisiana Agriculture*, vol. 37, No. 3, pp. 25–26 (1994).

Croughan, T., "Assessment of Imidazolidone–Resistant Rice," 87th Annual Research Report, Rice Research Station, 1995, pp. 491–525 (Sep. 1996).

Croughan, T., "Herbicide Resistant Rice," *Proc. 25th Rice Tech., Work. Groups*, p. 44 (1994).

Croughan, T., "Production of Rice Resistant to AHAS–Inhibiting Herbicides," Congress on Cell and Tissue Culture, Tissue Culture Association, *In Vitro*, vol. 30A, p. 60, Abstract P–1009 (Jun. 4–7, 1994).

Croughan, T. et al., "Applications of Biotechnology to Rice Improvement," *Proc. 25th Rice Tech. Work. Groups*, pp. 62–63 (1994).

Croughan, T. et al., "Rice and Wheat Improvement through Biotechnology," 85th *Annual Research Report, Rice Research Station*, 1993, pp. 116–156 (1994).

Croughan, T. et al., "Rice and Wheat Improvement through Biotechnology," USDA CRIS Report Accession No. 0150120 (for Fiscal Year 1994—actual publication date currently unknown).

Croughan, T. et al., "Rice Improvement through Biotechnology," 86th *Annual Research Report, Rice Research Station*, 1994, pp. 461–482 (Sep. 1995).

Croughan, T. et al., "Rice and Wheat Improvement through Biotechnology," 84th *Annual Research Report, Rice Research Station*, 1992, pp. 100–103 (1993).

(List continued on next page.)

*Primary Examiner*—Gary Benzion
(74) *Attorney, Agent, or Firm*—John H. Runnels

(57) ABSTRACT

Rice plants are disclosed with two separate, but synergistic mechanisms for resistance to herbicides that normally inhibit a plant's acetohydroxyacid synthase (AHAS) enzyme. The herbicide resistance of plants with both resistance mechanisms is substantially greater than one would expect from a simple combination of the two types of resistance. The first of the two resistance mechanisms is a metabolic pathway that is not fully understood, but that does not itself involve a mutant AHAS enzyme. The second resistance mechanism is a mutant AHAS enzyme, an enzyme that shows direct resistance to levels of herbicide that normally inhibit the enzyme, in both in vivo and in vitro assays. Besides controlling red rice, many AHAS-inhibiting herbicides also effectively control other weeds that are common in rice fields. Several of these herbicides have residual activity, so that a treatment controls both existing weeds as well as weeds that sprout later. No herbicide currently available for use on rice has residual activity against a broad spectrum of weeds including red rice. With effective residual activity against red rice and other weeds, rice producers now have a weed control system superior to those currently used.

20 Claims, No Drawings

OTHER PUBLICATIONS

Lee et al., "The Molecular Basis of Sulfonylurea Herbicide Resistance in Tobacco," The EMBO J., vol. 7, No. 5, pp. 1241–1248 (1988).

Mazer et al., "Isolation and Characterization of Plant Genes Coding for Acetolactate Synthase, the Target Enzyme for Two Classes of Herbicides," Plant Physiol., vol. 85, pp. 1110–1117 (1987).

Miki et al., "Transformation of *Brassica napus* canola cultivars with *Arabidopsis thaliana* Acetohydroxyacid Synthase Genes and Analysis of Herbicide Resistance," Theor. Appl. Genet., vol. 80, pp. 449–458 (1990).

Newhouse et al., "Mutations in corn (*Zea mays* L.) Conferring Resistance to Imidazolinone Herbicides," Theor. Appl. Genet., vol. 83, pp. 65–70 (1991).

Odell et al., "Comparison of Increased Expression of Wild–Type and Herbicide–Resistant Acetolactate Synthase Genes in Transgenic Plants, and Indication of Postranscriptional Limitation on Enzyme Activity," Plant Physiol. vol. 94, pp. 1647–1654 (1990).

Sathasivan et al., "Molecular Basis of Imidazolinone Herbicide Resistance in *Arabidopsis thaliana* var Columbia," Plant Physiol. vol. 97, pp. 1044–1050 (1991).

Sathasivan et al., "Nucleotide Sequence of a Mutant Acetolactate Synthase Gene from an Imidazolinone–resistant *Arabidopsis thaliana* var. Columbia," Nucleic Acids Research vol. 18, No. 8, p. 2188 (1990).

Saxena et al., "Herbicide Resistance in *Datura innoxia*," Plant Physiol., vol. 86, pp. 863–867 (1988).

Sebastian et al., "Soybean Mutants with Increased Tolerance for Sulfonylurea Herbicides," Crop. Sci., vol. 27, pp. 948–952 (1987).

Shimamoto et al., "Fertile Transgenic Rice Plants Regenerated from Transformed Protoplasts," Nature, vol. 338, pp. 274–276 (1989).

Singh, B.K. et al., "Assay of Acetohydroxyacid Synthase," *Analytical Biochemistry*, vol. 171, pp. 173–179 (1988).

Terakawa et al., "Rice Mutant Resistant to the Herbicide Bensulfuron Methyl (BSM) by in vitro Selection," Japan. J. Breed., vol. 42, pp. 267–275 (1992).

Wiersma et al., "Isolation, Expression and Phylogenetic Inheritance of an Acetolactate Synthase Gene from *Brassica napus*," Mol. Gen. Genet., vol. 219, pp. 413–420 (1989).

HERBICIDE RESISTANT RICE

This is a continuation of application Ser. No. 09/029,109, filed Feb. 1, 1999; now U.S. Pat. No. 5,952,553 which was a continued prosecution application of Ser. No. 09/029,109, which was the United States national stage of international application PCT/US97/07092, international filing date Apr. 28, 1997, 35 U.S.C. §371 date Feb. 18, 1998, now allowed with the issue fee paid; which was a continuation-in-part of application Ser. No. 08/639,793, filed Apr. 29, 1996, now U.S. Pat. No. 5,773,704.

TECHNICAL FIELD

This invention pertains to herbicide resistant rice, particularly to rice resistant to the herbicides imazethapyr, imazaquin, nicosulfuron, primisulfuron, sulfometuron, imazapyr, imazameth, imazamox, derivatives of these herbicides, or other herbicides that interfere with the plant enzyme acetohydroxyacid synthase.

BACKGROUND ART

The development of novel herbicide resistance in plants offers significant production and economic advantages. Rice production is frequently restricted by the prevalence of a weedy relative of rice that flourishes in commercial rice fields. The weed is commonly called "red rice," and belongs to the same species as cultivated rice (*Oryza sativa* L.). The genetic similarity of red rice and commercial rice has made herbicidal control of red rice difficult. The herbicides Ordram (molinate: S-ethyl hexahydro-1-H-azepine-1-carbothioate) and Bolero (thiobencarb: S-[(4-chlorophenyl)methyl] diethylcarbamothioate) offer partial suppression of red rice, but no herbicide that actually controls red rice can currently be used in rice fields because of the simultaneous sensitivity of commercial rice to such herbicides. The development of a mutant commercial rice that is resistant to a herbicide effective on red rice will greatly increase the ability to control red rice infestations.

Rice producers in the southern United States typically rotate rice crops with soybeans to help control red rice infestations. While this rotation is not usually desirable economically, it is frequently necessary because no herbicide is currently available to control red rice infestations selectively in commercial rice crops. During the soybean rotation, the producer has a broad range of available herbicides that may be used on red rice, so that rice may again be grown the following year. United States rice producers can lose $200–$300 per acre per year growing soybeans instead of rice, a potential loss affecting about 2.5 million acres annually. Additional losses in the United States estimated at $50 million per year ream the lower price paid by mills for grain shipments contaminated with red rice. Total economic losses due to red rice in southern United States rice production are estimated to be $500 to $750 million a year.

Rice producers typically use the herbicides propanil (trade name Stam) or molinate (trade name Ordram) to control weeds in rice production. Propanil has no residual activity. Molinate is toxic to fish. Neither of these herbicides controls red rice. Imazethapyr ((±)-2-[4,5-dihydro-4-methyl-4-(1-methylethyl)-5-oxo-1H-imidazol-2-yl]-5-ethyl-3-pyridinecarboxylic acid) offers an environmentally acceptable alternative to molinate, has the residual weed control activity that propanil lacks, and is a very effective herbicide on red rice. Imazethapyr also offers excellent control of other weeds important in rice production, including barnyardgrass. Barnyardgrass is a major weed in rice production, and is currently controlled with propanil or molinate. However, there are reports that barnyardgrass is developing resistance to propanil.

The total potential market for rice varieties that are resistant to a herbicide that can control red rice is about 5.3 million acres in the United States, and the market outside the United States is potentially much larger. World rice production occupies about 350 million acres. Red rice is a serious weed pest in rice production in the United States, Brazil, Australia, Spain, and in most other rice-producing countries. Herbicides that inhibit the enzyme acetohydroxyacid synthase would offer a number of advantages over currently available herbicides if they could be used in commercial rice production. Potential advantages include long residual activity against weeds, effective control of the more important weeds in rice production, including red rice, and relative environmental acceptability.

U.S. Pat. No. 4,761,373 describes the development of mutant herbicide-resistant maize plants through exposing tissue cultures to herbicide. The mutant maize plants were said to have an altered enzyme, namely acetohydroxyacid synthase, which conferred resistance to certain imidazolinone and sulfonamide herbicides.

Lee et al., "The Molecular Basis of Sulfonylurea Herbicide Resistance in Tobacco," The EMBO J., vol. 7, no. 5, pp. 1241–1248 (1988), describe the isolation and characterization from *Nicotiana tabacum* of mutant genes specifying herbicide resistant forms of acetolactate synthase (also known as acetohydroxyacid synthase), and the reintroduction of those genes into sensitive lines of tobacco.

Saxena et al., "Herbicide Resistance in Datura innoxia," Plant Physiol., vol. 86, pp. 863–867 (1988) describe several *Datura innoxia* lines resistant to sulfonylurea herbicides, some of which were also found to be cross-resistant to imidazolinone herbicides.

Mazur et al., "Isolation and Characterization of Plant Genes Coding for Acetolactate Synthase, the Target Enzyme for Two Classes of Herbicides," Plant Physiol. vol. 85, pp. 1110–1117 (1987), discuss investigations into the degree of homology among acetolactate synthases from different species.

Reference is also made to commonly-assigned U.S. patent application Ser. No. 07/657,429, filed Feb. 19, 1991, disclosing transformed plants with genetically engineered imidazolinone resistance, conferred through a gene cloned from a plant such as a mutated *Arabidopsis thaliana*. See also a related paper, Sathasivan et al., "Nucleotide Sequence of a Mutant Acetolactate Synthase Gene from an Imidazolinone-resistant *Arabidopsis thaliana* var. *Columbia*," Nucleic Acids Research vol. 18, no. 8, p. 2188 (1990).

Examples of herbicide-resistant AHAS enzymes in plants other than rice are disclosed in U.S. Pat. No. 5,013,659; K. Newhouse et al., "Mutations in corn (*Zea mays* L.) Conferring Resistance to Imidazolinone Herbicides," Theor. Appl. Genet., vol. 83, pp. 65–70 (1991); K. Sathasivan et al., "Molecular Basis of Imidazolinone Herbicide Resistance in *Arabidopsis thaliana* var *Columbia*," Plant Physiol. vol. 97, pp. 1044–1050 (1991); B. Miki et al., "Transformation of *Brassica napus* canola cultivars with *Arabidopsis thaliana* Acetohydroxyacid Synthase Genes and Analysis of Herbicide Resistance," Theor. Appl. Genet., vol. 80, pp. 449–458 (1990); P. Wiersma et al., "Isolation, Expression and Phylogenetic Inheritance of an Acetolactate Synthase Gene from *Brassica napus*," Mol. Gen. Genet., vol. 219, pp. 413–420 (1989); and J. Odell et al., "Comparison of Increased Expression of Wild-Type and Herbicide-Resistant Acetolactate Synthase Genes in Transgenic Plants, and Indication of Postranscriptional Limitation on Enzyme Activity," Plant Physiol., vol. 94, pp. 1647–1654 (1990).

S. Sebastian et al., "Soybean Mutants with Increased Tolerance for Sulfonylurea Herbicides," Crop. Sci., vol. 27, pp. 948–952 (1987) discloses soybean mutants resistant to sulfonylurea herbicides through a mechanism other than an altered form of the AHAS enzyme.

K. Shimamoto et al., "Fertile Transgenic Rice Plants Regenerated from Transformed Protoplasts," Nature, vol. 338, pp. 274–276 (1989) discloses a genetic transformation protocol in which electroporation of protoplasts was used to transform a gene encoding β-glucuronidase into rice.

T. Terakawa et al., "Rice Mutant Resistant to the Herbicide Bensulfuron Methyl (BSM) by in vitro Selection," Japan. J. Breed., vol. 42, pp. 267–275 (1992) discloses a rice mutant resistant to a sulfonylurea herbicide, derived by selective pressure on callus tissue culture. Resistance was attributed to a mutant AHAS enzyme.

Following are publications by the inventor (or the inventor and other authors) concerning research on herbicide-resistant rice varieties. These publications are T. Croughan et al., "Rice and Wheat Improvement through Biotechnology," 84*th Annual Research Report, Rice Research Station*, 1992, pp. 100–103 (1993); T. Croughan et al., "Rice and Wheat Improvement through Biotechnology," 85*th Annual Research Report, Rice Research Station*, 1993, pp. 116–156 (1994); T. Croughan, "Application of Tissue Culture Techniques to the Development of Herbicide Resistant Rice," *Louisiana Agriculture*, vol. 37, no. 3, pp. 25–26 (1994); and T. Croughan et al., "Rice Improvement through Biotechnology," 86*th Annual Research Report, Rice Research Station*, 1994, pp. 461–482 (September 1995). (Note that the Annual Research Reports of the Rice Research Station are published in the year after the calendar year for which activities are reported. For example, the 84*th Annual Research Report, Rice Research Station*, 1992, summarizing research conducted in 1992, was published in 1993.)

Following are two commonly-assigned United States patent applications concerning herbicide resistant rice, also filed by the present inventor: Ser. No. 08/345,213, filed Nov. 28, 1994, now U.S. Pat. No. 5,545,822; and Ser. No. 08/628,031, filed Apr. 4, 1996.

DISCLOSURE OF INVENTION

In the present invention, novel herbicide resistance has been developed and expressed in rice plants. The novel rice is believed to be the first to have both pre-emergence and post-emergence resistance to herbicides that are effective against red rice. The novel rice either has demonstrated resistance, or is expected to demonstrate resistance, to each of the following herbicides: imazethapyr, imazaquin, nicosulfuron, primisulfuron, sulfometuron, imazapyr, imazameth, and imazamox. The novel rice is also expected to be resistant to derivatives of these herbicides, and to at least some of the other herbicides that normally inhibit acetohydroxyacid synthase (AHAS), particularly imidazolinone and sulfonylurea herbicides. The herbicidal activity of each of the above herbicides is known to be due to its effect on the acetohydroxyacid synthase (AHAS) enzyme. This enzyme catalyzes the first step in the synthesis of the amino acids leucine, valine, and isoleucine. Inhibition of the AHAS enzyme is normally fatal to plants.

Rice plants in accordance with this invention have two separate mechanisms for resistance to herbicides that normally inhibit AHAS. It has been unexpectedly discovered that incorporating the two herbicide resistance mechanisms into a single plant is synergistic—the herbicide resistance of plants with both mechanisms is substantially greater than one would expect from a simple combination of the two types of resistance.

The first of the two resistance mechanisms is a metabolic pathway that is not fully understood, but that does not itself involve a mutant AHAS enzyme. The first mechanism confers herbicide resistance even to plants with a wild-type, non-resistant AHAS enzyme. The second resistance mechanism is a mutant AHAS enzyme, an enzyme that shows direct resistance to levels of herbicide that normally inhibit the enzyme, in both in vivo and in vitro assays.

The synergism from combining the two resistance mechanisms was striking. Positive control, non-resistant rice plants were completely killed by herbicide applied at a rate equivalent to 0.063 pounds active ingredient imazethapyr per acre (the recommended rate for controlling weeds). By contrast, plants having both resistance mechanisms showed no visible injury 36 days after treatment, even when sprayed with five times that level of imazethapyr (0.313 pounds active ingredient per acre). Thirty-six days after treatment, the hybrids had a rating of 10 on a 0–10 scale, in which "0" denoted a dead plant, and "10" denoted no visible injury, equivalent to a negative control plant sprayed with no herbicide. For comparison, at the same treatment level (0.313 lb a.i./acre) plants with only one of the two resistance mechanisms exhibited substantial injury 36 days after treatment. Plants with only the first resistance mechanism had a rating of about 0.6 on the same 10-point scale, and plants having only the second resistance mechanism had a rating of about 4.0. It was totally unexpected that plants with both resistance mechanisms should exhibit no herbicide injury at all under conditions that caused substantial injury to plants having either single resistance mechanism.

Besides controlling red rice, many AHAS-inhibiting herbicides also effectively control other weeds commonly found in rice fields. Several of these herbicides have residual activity, so that a treatment controls both existing weeds as well as weeds that sprout later—a point that has significant consequences for rice production. No herbicide currently available for use on rice has residual activity against a broad spectrum of weeds including red rice. With effective residual activity against red rice and other weeds, rice producers now have a weed control system far superior to those currently used.

One role of water in rice production is in weed control—a layer of standing water in the rice field inhibits the growth of weeds. With a herbicide having residual weed control properties, producers will have much greater flexibility in water management. Flooding of fields may now be delayed, which in turn will help control the rice water weevil, the primary insect pest of rice. Alternatively, or perhaps in conjunction, pumping costs could be reduced by delaying flooding until sufficient rain falls to flood a field at no cost to the producer.

MODES FOR CARRYING OUT THE INVENTION

Resistance Mechanism 1

The first resistance mechanism of the synergistic combination is a metabolic-based resistance that has not been fully characterized, but that acts independently of the AHAS enzyme. This first herbicide resistance mechanism is that expressed by the rice plant having ATCC accession number 75295.

Rice plants having the first resistance mechanism were developed through anther culture. Anther culture is a technique that can cause genetic variability among clones. The cells were not exposed to herbicide while in culture. Rather, progeny of plants grown up from the cultures were exposed to herbicide in field conditions. While screening for herbicide resistance at the cellular level has the advantage of screening far greater numbers of individual genomes, there are advantages to initial testing in the field, as was done here. In particular, there may not always be correspondence between the characteristics expressed by plant cells growing in culture and the traits of whole plants grown in field conditions.

This resistant line was derived by conducting anther culture on the $F_2$ progeny of a backcross made by pollinating a rice plant of the variety "Lemont" with pollen from the rice variety "Mercury," followed by a backcross using pollen from this hybrid to pollinate a plant of the variety "Mercury." The resulting backcross is described as Mercury// Lemont/Mercury. Anthers collected from a plant resulting from this backcross were plated on callus induction medium, and the resulting calli were transferred to plant regeneration media. The procedures used were generally as described in Croughan and Chu, "Rice (*Oryza sativa* L.): Establishment of Callus Cultures and the Regeneration of Plants" in Bajaj (Ed.), "Biotechnology in Agriculture and Forestry," pp. 19–37 (1991). Several regenerated plants were produced and grown to maturity in a greenhouse to produce seed. Progeny seed were planted in an open field, and herbicide applications were made using a garden tractor-mounted spray rig.

A set of 4,193 progeny rows derived from this anther culture procedure were planted in an open field, and were sprayed with 4 ounces per acre of Pursuit (1.00 ounce active ingredient imazethapyr per acre) at the four-leaf stage of seedling development. All rows but one were injured or killed. One row showed no apparent symptoms, however. Four weeks after the initial treatment, part of the resistant row was removed from the test site as a precaution, and the entire test site was then sprayed with 8 ounces/acre Pursuit (2.00 ounces active ingredient imazethapyr per acre). This treatment was lethal to all the rows that survived the initial spraying (but in an injured state), and again induced no apparent symptoms in the resistant line.

To maximize seed production, individual plants from the resistant row were separated and transplanted at a wide spacing. All the plants proved fertile. Approximately 7 pounds of fertile seed were harvested from the resistant plants at maturity.

The resistance of these plants to several other AHAS-inhibiting herbicides was also tested. Nine-foot-long field plots were planted with seven rows of rice per plot. The test included nine check rice varieties, and the ATCC 75295 rice line. A shielded spray boom was used to apply herbicide, spraying six of the seven rows in each plot. The four herbicides used were Pursuit (imazethapyr: (±)-2-[4,5-dihydro-4-methyl-4-(1-methylethyl)-5-oxo-1H-imidazol-2-yl]-5-ethyl-3-pyridinecarboxylic acid); Scepter (imazaquin: 2-[4,5-dihydro-4-methyl-4-(1-methylethyl)-5-oxo-1H-imidazol-2-yl]-3-quinolinecarboxylic acid); Accent (nicosulfuron: 2-(((((4,6-dimethoxypyrimidin-2-yl) aminocarbonyl))aminosulfonyl))-N,N-dimethyl-3-pyridinecarboxamide); and Beacon (primisulfuron: 3-[4,6-bis (difluoromethoxy)-pyrimidin-2-yl]-1-(2-methoxycarbonylphenylsulfonyl)urea). The herbicides were applied to two replicate plots for each herbicide when the rice was at the three-leaf stage of maturity. Two replicate plots of each check variety and of the resistant line were left unsprayed as controls. The Accent treatment used 0.67 ounce of product (0.50 ounce active ingredient) per acre, with 0.25% nonionic surfactant. The Pursuit treatment used four ounces of product (1.00 ounce active ingredient) per acre, with 0.25% nonionic surfactant. The Scepter treatment used one pint of product (3.00 ounces active ingredient) per acre, with 0.25% nonionic surfactant. The Beacon treatment used 0.76 ounce of product (0.57 ounce active ingredient) per acre, with 0.25% nonionic surfactant. The check plots all showed extensive injury or complete death from the herbicide treatments. The herbicide resistant line showed excellent resistance to Accent, and good resistance to Scepter and Pursuit. Resistance to Beacon was lower, but still significantly greater than that of the check rice varieties. A similar test with the same rice varieties and the ATCC 75295 line was conducted at the five-leaf stage of development (i.e., plants fifteen days older than in the test described above), using Accent, Scepter, and Pursuit at the rates given above. The check plots again showed extensive injury or complete death from the herbicide treatments. The ATCC 75295 line again showed excellent resistance to Accent, and good resistance to Scepter and Pursuit. In subsequent tests, this line also exhibited resistance to Arsenal (imazapyr) and Cadre (imazameth). The ATCC 75295 line was resistant only when herbicide was applied post-emergence.

Assays of the AHAS enzyme expressed by the ATCC 75295 rice line demonstrated that the first mechanism of resistance acts independently of the AHAS enzyme, and that the mechanism provides protection even where the AHAS enzyme itself is susceptible to the herbicide and is not over-expressed.

The herbicide resistance of the AHAS enzyme from the ATCC 75295 rice line was compared to the resistance of the AHAS enzymes from the rice varieties "Lemont" and "Mercury," the varieties that were the ancestors of this rice line. The procedures used to assay the activity of acetohydroxyacid synthase were substantially as described in B. K. Singh et al., "Assay of Acetohydroxyacid Synthase," *Analytical Biochemistry*, vol. 171, pp. 173–179 (1988), except as noted. In the first paragraph of Singh's "Materials and Methods," instead of corn suspension culture cells, stem tissues from greenhouse-grown rice seedlings at the four-leaf stage of development were used. Leaf blades were removed, and 40.0 grams (fresh weight) of tissue were extracted in the same manner for each of the three varieties. At the suggestion of the first author, B. K. Singh (personal communication), the desalting step mentioned at the bottom of Singh's first column under "Materials and Methods" was eliminated. Pursuit herbicide (imazethapyr) was included in the "standard reaction mixture" for the AHAS assay in the concentrations indicated in Table 1 below. Checks were made of direct acetoin formation during the enzyme assay. Each treatment was conducted with two replicates.

As is shown in Table 1 (which expresses enzyme activities as a percentage of control), the Lemont AHAS enzyme showed the greatest resistance to imazethapyr, followed by that of Mercury, and the AHAS from the ATCC 75295 rice line had the greatest susceptibility to the imazethapyr treatment, at least at the highest concentration of herbicide tested. Colorimetric absorbance at 520 nm in the absence of herbicide showed that Lemont and the deposited rice line had about the same uninhibited AHAS activity, while Mercury had slightly less activity (data not shown). This observation shows that the resistance of the ATCC 75295 line was not due to higher levels of expression of the AHAS enzyme, but instead resulted from some other factor. This other factor is currently unknown, but is believed perhaps to involve an AHAS-independent pathway for metabolism of herbicide.

TABLE 1

Effect of Imazethapyr on AHAS Activity in Enzyme Extracts from Normal Rice (Varieties Lemont and Mercury) and from Rice Line ATCC 75295. Activities Expressed as Percent of Control.

| Concentration of Imazethapyr | Variety | | |
|---|---|---|---|
| [$\mu$M] | Lemont | Mercury | ATCC 75295 |
| 0 | 100[a] | 100[a] | 100[a] |
| 0.1 | 102[a] | 100[a] | 102[a] |
| 1 | 102[a] | 89[b] | 89[b] |
| 10 | 87[b] | 64[d] | 61[d] |
| 100 | 81[c] | 62[d] | 48[e] |

Values followed by the same letter in Table 1 were not significantly different from one another (P < 0.05) (DMRT).

A sample of the rice seeds having this first resistance mechanism was deposited with the American Type Culture Collection (ATCC), 12301 Parklawn Drive, Rockville, Md. 20852 on Aug. 20, 1992, and was assigned ATCC Accession No. 75295. This deposit was made pursuant to a contract between ATCC and the assignee of this patent application, Board of Supervisors of Louisiana State University and Agricultural and Mechanical College. The contract with ATCC provides for permanent and unrestricted availability of these seeds or the progeny of these seeds to the public on the issuance of the U.S. patent describing and identifying the deposit or the publication or the laying open to the public of any U.S. or foreign patent application, whichever comes first, and for availability of these seeds to one determined by the U.S. Commissioner of Patents and Trademarks to be entitled thereto under pertinent statutes and regulations. The assignee of the present application has agreed that if the seeds on deposit should become nonviable or be lost or destroyed when cultivated under suitable conditions, they will be promptly replaced on notification with a viable sample of the same seeds.

Resistance Mechanism 2

The second resistance mechanism results from a herbicide-resistant AHAS enzyme. The preferred resistant AHAS enzyme is that expressed by the rice plant having ATCC accession number 97523. Rice plants expressing this mutant enzyme have been shown to have desirable herbicide resistance properties in both greenhouse and field trials.

The second resistance mechanism resulted from inducing mutations in seeds of each of ten rice varieties. Mutations were induced by exposure either to gamma rays or to the chemical mutagen ethyl methanesulfonate (EMS). Ten-pound lots of seed of each variety were subjected to 25 k-rad of gamma irradiation from a Cobalt-60 source at the Nuclear Science Center, Louisiana State University, Baton Rouge, La. prior to planting. An additional ten pounds of seed of each variety was divided into three equal portions; and each portion was soaked for 16 hours in either 0.1%, 0.5%, or 1% EMS immediately prior to planting. Several hundred pounds of seed were harvested from plants grown from the seeds subjected to these mutagenic treatments.

The following spring the harvested seed was planted in strips in a field planting occupying a total of about three acres. At the 3–4 leaf stage of seedling development, herbicides were applied to screen for herbicide-resistant mutants. Half of the seedlings of each variety were sprayed with a 2× treatment of nicosulfuron, and half were sprayed with a 2× treatment of imazethapyr, in both cases by a tractor-mounted sprayer. Nicosulfuron was applied at the rate of 0.063 lb active ingredient (a.i.) per acre, and imazethapyr was applied at 0.125 lb a.i. per acre. Non-ionic surfactant (0.25%) was added to each spray solution. Approximately 35 million rice seedlings were sprayed in this manner. About four weeks later a single surviving plant was identified. The surviving plant was in a strip that had been sprayed with imazethapyr, and was derived from the "parent" rice variety "AS3510," treated by exposure to 0.5% EMS. No symptoms of injury from the herbicide treatment were evident on this plant at the time it was discovered, while all the other plants were either severely injured or dead. The plant was transferred to the greenhouse for seed increase and further testing.

Subsequent testing in the greenhouse and field demonstrated that the progeny of this rice plant possess resistance to several AHAS-inhibiting herbicides, including at least the following herbicides: imazethapyr, nicosulfuron, imazaquin, imazameth, imazapyr, and imazamox. (Imazamox is sold by American Cyanamid under the trade name Raptor, and has as active ingredient (+)-5-methoxymethyl-2-(4-isopropyl-4-methyl-5-oxo-2-imidazolin-2-yl) nicotinic acid. Imazameth is sold by American Cyanamid under the trade name Cadre, and has as active ingredient (±)-2-[4,5-dihydro-4-methyl-4-(1-methyl-ethyl)-5-oxo-1H-imidazol-2-yl]-5-methyl-3-pyridinecarboxylic acid; alternate chemical name (±)-2-(4-isopropyl-4-methyl-5-oxo-2-imidazolin-2-yl)-5-methylnicotinic acid). Imazapyr is sold by American Cyanamid under the trade name Arsenal, and has active ingredient 2-[4,5-dihydro-4-methyl-4-(1-methylethyl)-5-oxo-1H-imidazol-2-yl]-3-pyridinecarboxylic acid) This line is resistant to herbicides applied either pre-emergence or post-emergence. AHAS enzyme assays indicated that, unlike the case for the first herbicide resistance mechanism, this rice line possesses a mutant AHAS enzyme that is responsible for resistance to AHAS-inhibiting herbicides.

A sample of the rice seeds having this preferred second resistance mechanism was deposited with the American Type Culture Collection (ATCC), 12301 Parklawn Drive, Rockville, Md. 20852 on Apr. 25, 1996, and was assigned ATCC Accession No. 97523. This deposit was made pursuant to a contract between ATCC and the assignee of this patent application, Board of Supervisors of Louisiana State University and Agricultural and Mechanical College. The contract with ATCC provides for permanent and unrestricted availability of these seeds or the progeny of these seeds to the public on the issuance of the U.S. patent describing and identifying the deposit or the publication or the laying open to the public of any U.S. or foreign patent application, whichever comes first, and for availability of these seeds to one determined by the U.S. Commissioner of Patents and Trademarks to be entitled thereto under pertinent statutes and regulations. The assignee of the present application has agreed that if the seeds on deposit should become nonviable or be lost or destroyed when cultivated under suitable conditions, they will be promptly replaced on notification with a viable sample of the same seeds.

Although it is preferred that the two resistance mechanisms be used in combination as discussed in the following section, even when used alone this second resistance mechanism has superior properties over previously known mechanisms for herbicide resistance in rice, and therefore could be used in commercial rice varieties as the sole mechanism for herbicide resistance.

The Synergistic Combination.

Hybrids of the rice lines ATCC 97523 and ATCC 75295 were produced by cross-pollination. Greenhouse tests showed a synergistic effect on herbicide resistance. The resistance of the hybrids was substantially greater than would be expected from a simple combination of the individual resistance levels.

In the greenhouse tests, pots were planted with $F_3$ seed from crosses between the two lines. Each pot was planted with seed from a single panicle from a single plant; each pot was therefore the equivalent of a headrow. A total of 140 pots were planted in er, along with 40 pots of various non-resistant genotypes for comparison. Imazethapyr was applied at the 2–3 leaf stage two weeks after planting, at rates equivalent to 0.063 lb. active ingredient (a.i.) per acre, 0.125 lb. a.i./acre, and 0.313 lb. a.i./acre.

Because the material being tested was an $F_3$ population, with genes still segregating, individual plants had different levels of resistance. At the time this patent application is being filed, there had not been sufficient time to raise rice lines that were demonstrably homozygous for both resistance mechanisms. Raising such demonstrably homozygous lines will be routine for one of ordinary skill in the art, but will require additional time.

Some $F_3$ plants inherited no genes for resistance, and were as susceptible as the check varieties, suffering 100% mortality in all treatments. At the other end of the spectrum were plants that inherited both resistance mechanisms, and that exhibited tolerance to all levels of herbicide tested, including the highest 0.313 lb. a.i. per acre treatment. The resistance of these plants was substantially higher than the resistance of either parent line, and was also substantially higher than would be expected from a simple combination of the two resistance levels.

The synergism from combining the two resistance mechanisms was striking. Positive control, non-resistant rice plants were completely killed by herbicide applied at a rate equivalent to 0.063 pounds active ingredient imazethapyr per acre. By contrast, plants having both resistance mechanisms showed no visible injury 36 days after treatment, even when sprayed with the highest level of imazethapyr tested (0.313 pounds active ingredient per acre). These hybrids had a rating of 10 on a 0–10 scale, in which "0" denoted a dead plant, and "10" denoted no visible injury, equivalent to a negative control plant sprayed with no herbicide. For comparison, at the same treatment level (0.313 lb a.i./acre) plants with only one of the two resistance mechanisms exhibited substantial injury 36 days after treatment. Plants with only the first resistance mechanism had a rating of about 0.6 on the same 10-point scale, and plants having only the second resistance mechanism had a rating of about 4.0. (See the far right column in Table 2 below.) It was totally unexpected that plants with both resistance mechanisms should exhibit no herbicide injury at all under conditions that caused substantial injury to plants having either single resistance mechanism alone.

Table 2 summarizes measurements taken 36 days after spraying rice at the 2–3 leaf stage of development.

TABLE 2

Ratings of Rice Plant Vigor 36 Days after Treatment with Various Levels of Imazethapyr, on a 10-point scale

| Rice Line | 0 (Control) | Imazethapyr Concentration | | |
| --- | --- | --- | --- | --- |
| | | 0.063 lb. a.i./acre | 0.125 lb. a.i./acre | 0.313 lb. a.i./acre |
| Non-Resistant Control* | 10 | 0.33 ± 0.18 | 0.12 ± 0.06 | 0.15 ± 0.15 |
| ATCC 75295 | 10 | 0.61 ± 0.03 | 0.81 ± 0.45 | 0.55 ± 0.55 |
| ATCC 97523 | 10 | 9.01 ± 0.59 | 5.71 ± 0.93 | 4.00 ± 0.32 |
| Resistant $F_3$ Hybrid of ATCC 75295 and ATCC 97523 | 10 | 10 | 10 | 10 |

*Note: All non-resistant controls were killed by application of imazethapyr at each of the non-zero rates listed in Table 1. Imazethapyr is a slow-acting herbicide. When the above ratings were assigned 36 days after treatment, a few non-resistant control plants lingered in a greatly weakened state, and died subsequently.

It was also observed that the resistant $F_3$ plants recovered from the herbicide application and resumed growth much more quickly. The resistant $F_3$ plants began visible resumption of growth within about a week of herbicide application, while ATCC 97523 plants required about two weeks, and ATCC 75295 plants required about three weeks to resume visible growth.

Field tests of the two "parent" lines, and of the $F_3$ hybrids confirmed the greenhouse studies. Several thousand headrows were planted in blocks of 1000 rows each. Check varieties were interspersed, including both the parent varieties ATCC 97523 and ATCC 75295, as well as several non-resistant cultivars. Blocks were sprayed with different AHAS-inhibiting herbicides at various strengths and at various stages of development.

Once progeny are identified that are demonstrably homozygous for both resistance mechanisms, those progeny will be used to breed varieties for commercial use. Crossing the homozygous resistant rice with established varieties or cultivars through standard means will yield herbicide-resistant rice varieties and hybrids with good productivity and other commercially desirable properties.

Other genes encoding herbicide resistant AHAS enzymes may be used in place of the preferred resistant AHAS enzyme from rice line ATCC 97523 in the synergistic combination. Any of these genes may be transformed into rice plants through plant genetic transformation protocols that are well known in the art. Several such genes are known in the art, and include those, for example, disclosed in U.S. Pat. No. 4,761,373; Lee et al., "The Molecular Basis of Sulfonylurea Herbicide Resistance in Tobacco," The EMBO J., vol. 7, no. 5, pp. 1241–1248 (1988); Saxena et al., "Herbicide Resistance in *Datura innoxia*," Plant Physiol., vol. 86, pp. 863–867 (1988); U.S. patent application Ser. No. 07/657,429; Sathasivan et al., "Nucleotide Sequence of a Mutant Acetolactate Synthase Gene from an Imidazolinone-resistant *Arabidopsis thaliana* var. *Columbia*," Nucleic Acids Research vol. 18, no. 8, p. 2188 (1990); U.S. Pat. No. 5,013,659; K. Newhouse et al., "Mutations in corn (*Zea mays* L.) Conferring Resistance to Imidazolinone Herbicides," Theor. Appl. Genet., vol. 83, pp. 65–70 (1991); K. Sathasivan et al., "Molecular Basis of imidazolinone Herbicide Resistance in *Arabidopsis thaliana* var *Columbia*," Plant Physiol. vol. 97, pp. 1044–1050 (1991); B. Miki et al., "Transformation of *Brassica napus* canola cultivars with *Arabidopsis thaliana* Acetohydroxyacid Synthase Genes and Analysis of Herbicide Resistance," Theor. Appl. Genet., vol. 80, pp. 449–458 (1990); P. Wiersma et al., "Isolation, Expression and Phylogenetic Inheritance of an Acetolactate Synthase Gene from *Brassica napus*," Mol. Gen. Genet., vol. 219, pp. 413–420 (1989); J. Odell et al., "Comparison of Increased Expression of Wild-Type and Herbicide-Resistant Acetolactate Synthase Genes in Transgenic Plants, and Indication of Postranscriptional Limitation on Enzyme Activity," Plant Physiol., vol. 94, pp. 1647–1654 (1990); and T.

Terakawa et al., "Rice Mutant Resistant to the Herbicide Bensulfuron Methyl (BSM) by in vitro Selection," Japan. J. Breed., vol. 42, pp. 267–275 (1992).

Miscellaneous

Because red rice and commercial rice belong to the same species, the planting of a herbicide-resistant commercial rice crop entails some risk that herbicide resistance would be transferred to red rice. However, rice is self-pollinating, and the frequency of outcrossing is low, even between immediately adjacent plants flowering in synchrony. The likelihood of transferring resistance to red rice could be minimized by breeding resistant varieties that flower significantly earlier than does red rice (e.g., using conventional breeding techniques, or by further anther culture). Serendipitously, the "parent" line ATCC 97523 matures very early; in fact, its seeds are ready for harvest before red rice even begins to flower. Maintaining this early-maturing phenotype in resistant varieties developed from the hybrid rice line will be desirable to reduce the likelihood of outcrossing to red rice.

If a strain of red rice should nevertheless develop that is resistant to the same herbicides as the resistant commercial rice, the plants can always be treated with a broad range of other available herbicides—particularly if the resistant red rice were discovered early, before having much opportunity to propagate.

Because imazethapyr, imazaquin, nicosulfuron, primisulfuron, imazameth, imazamox, and imazapyr inhibit the activity of acetohydroxyacid synthase, and because resistance to each of these herbicides has been demonstrated in ATCC 75295, ATCC 97523, or their novel herbicide-resistant hybrid, it is expected that the novel herbicide resistant rice will show resistance to other herbicides that normally inhibit this enzyme. In addition to those discussed above, such herbicides include at least the following: sulfometuron (trade name Oust, chemical name 2-[[[[(4,6-dimethyl-2-pyrimidinyl)amino]carbonyl]amino]sulfonyl] benzoic acid methyl ester); metsulfuron methyl (trade name Ally, chemical name methyl 2-[[[[(4-methoxy-6-methyl-1,3,5-triazin-2-yl)amino]carbonyl]amino]sulfonyl]benzoate); mixture of thifensulfuron methyl and tribenuron methyl (trade name Harmony Extra, mixture of methyl-3-[[[[(4-methoxy-6-methyl-1,3,5-triazin-2-yl)amino]carbonyl]amino]sulfonyl]-2-thiophenecarboxylate and methyl-2-[[[[N-(4-methoxy-6-methyl-1,3,5-triazin-2-yl)methylamino]carbonyl]amino]sulfonyl]benzoate); thifensulfuron methyl (trade name Pinnacle, chemical name methyl-3-[[[[(4-methoxy-6-methyl-1,3,5-triazin-2-yl)amino]carbonyl]amino]sulfonyl]-2-thiophenecarboxylate); chlorsulfuron (trade name Glean or Telar, chemical name 2-chloro-N-[(4-methoxy-6-methyl-1,3,5-triazin-2-yl)aminocarbonyl]benzenesulfonamide); chlorimuron ethyl (trade name Classic, chemical name ethyl 2-[[[[(4-chloro-6-methoxypyrimidin-2-yl)amino]carbonyl]amino]sulfonyl benzoate); tribenuron methyl (trade name Express, chemical name methyl 2-[[[[N-(4-methoxy-6-methyl-1,3,5-triazin-2-yl)methylamino]carbonyl]amino]sulfonyl benzoate); imazamethabenz methyl (trade name Assert, chemical name m-toluic acid, 6-(4-isopropyl-4-methyl-5-oxo-2-imidazolin-2-yl)-, methyl ester; and p-toluic acid, 2-(4-isopropyl-4-methyl-5-oxo-2-imidazolin-2-yl)-, methyl ester); and triasulfuron (trade name Amber, chemical name 3-(6-methoxy-4-methyl-1,3,5-triazin-2-yl)-1-[2-(2-chloroethoxy)-phenylsulfonyl]-urea.

Preliminary results from tests that are underway as of the date this application is being filed showed that the novel rice plants exhibited at least some resistance to the herbicides Oust, Ally, Pinnacle, Glean, Express, and Amber.

As used in the claims below, unless otherwise clearly indicated by context, the term "rice plant" is intended to encompass rice plants at any stage of maturity, as well as any cells, tissues, or organs taken or derived from any such plant, including without limitation any seeds, leaves, stems, flowers, roots, single cells, gametes, anther cultures, tissue cultures, or protoplasts.

The complete disclosures of all references cited in this specification are hereby incorporated by reference. In the event of an otherwise irreconcilable conflict, however, the present specification shall control.

What is claimed:

1. A process for controlling weeds in the vicinity of a rice plant, said process comprising applying a herbicide to the weeds and to the rice plant, wherein the herbicide normally inhibits acetohydroxyacid synthase, at levels of the herbicide that would normally inhibit the growth of a rice plant, and wherein:
    (a) the growth of the rice plant is resistant to inhibition by the herbicide at levels of the herbicide that would normally inhibit the growth of a rice plant; and
    (b) the rice plant is a derivative of the plant with ATCC accession number 97523; and
    (c) the rice plant has the herbicide resistance characteristics of the plant with ATCC accession number 97523.

2. A process as recited in claim 1, wherein the herbicide comprises a herbicidally effective imidazolinone.

3. A process as recited in claim 2, wherein the herbicide comprises imazamethabenz methyl.

4. A process as recited in claim 1, wherein the herbicide comprises a herbicidally effective sulfonylurea.

5. A process as recited in claim 4, wherein the herbicide comprises metsulfuron methyl.

6. A process as recited in claim 4, wherein the herbicide comprises tribenuron methyl.

7. A process as recited in claim 4, wherein the herbicide comprises triasulfuron.

8. A process as recited in claim 4, wherein the herbicide comprises thifensulfuron methyl.

9. A process as recited in claim 4, wherein the herbicide comprises chlorsulfuron.

10. A process as recited in claim 4, wherein the herbicide comprises chlorimuron ethyl.

11. A process for controlling weeds in the vicinity of a rice plant, said process comprising applying a herbicide to the weeds and to the rice plant, wherein the herbicide normally inhibits acetohydroxyacid synthase, at levels of the herbicide that would normally inhibit the growth of a rice plant, and wherein:
    (a) the growth of the rice plant is resistant to inhibition by the herbicide at levels of the herbicide that would normally inhibit the growth of a rice plant; and
    (b) the rice plant is a derivative both of the plant with ATCC accession number 75295, and of the plant with ATCC accession number 97523; and
    (c) the rice plant has the herbicide resistance characteristics both of the plant with ATCC accession number 75295, and of the plant with ATCC accession number 97523.

12. A process as recited in claim 11, wherein the herbicide comprises a herbicidally effective imidazolinone.

13. A process as recited in claim 12, wherein the herbicide comprises imazamethabenz methyl.

14. A process as recited in claim 11, wherein the herbicide comprises a herbicidally effective sulfonylurea.

15. A process as recited in claim 14, wherein the herbicide comprises metsulfuron methyl.

16. A process as recited in claim 14, wherein the herbicide comprises tribenuron methyl.

17. A process as recited in claim 14, wherein the herbicide comprises triasulfuron.

18. A process as recited in claim 14, wherein the herbicide comprises thifensulfuron methyl.

19. A process as recited in claim 14, wherein the herbicide comprises chlorsulfuron.

20. A process as recited in claim 14, wherein the herbicide comprises chlorimuron ethyl.

\* \* \* \* \*

UNITED STATES PATENT AND TRADEMARK OFFICE
CERTIFICATE OF CORRECTION

PATENT NO.   : 6,274,796 B1
DATED        : August 14, 2001
INVENTOR(S)  : Timothy P. Croughan It is certified that error appears in the above-identified patent and that said Letters Patent is hereby corrected as shown below:

Column 1,
Line 52, "ream" should read -- result from --.

Column 9,
Line 9, "er," should read -- this manner, --.

Signed and Sealed this

Twelfth Day of March, 2002

*Attest:*

*Attesting Officer*

JAMES E. ROGAN
*Director of the United States Patent and Trademark Office*